United States Patent [19]

Cottingham

[11] Patent Number: 4,597,944
[45] Date of Patent: Jul. 1, 1986

[54] AGGLUTINATION REAGENT DETECTION SYSTEM

[76] Inventor: Hugh V. Cottingham, 49 Mountain Ave., Caldwell, N.J. 07006

[21] Appl. No.: 542,846

[22] Filed: Oct. 18, 1983

[51] Int. Cl.<sup>4</sup> ............... G01N 21/49; G01N 33/48
[52] U.S. Cl. ............................ 422/73; 356/338
[58] Field of Search ............ 422/67, 68, 73, 102; 356/338-340; 436/520, 524, 809; 435/300, 301; 350/536; 250/461.2; 366/101

[56] References Cited

U.S. PATENT DOCUMENTS

| | | | |
|---|---|---|---|
| 3,065,665 | 11/1962 | Akhtar et al. | 356/341 |
| 3,398,935 | 8/1968 | Livesey et al. | 366/101 |
| 3,656,833 | 4/1972 | Wallace | 350/95 |
| 3,736,042 | 5/1973 | Markovits et al. | 350/536 |
| 3,819,271 | 6/1974 | Beug et al. | 356/246 X |
| 3,904,781 | 9/1975 | Henry | 350/536 |
| 3,905,767 | 9/1975 | Morris et al. | 356/340 |
| 4,055,768 | 10/1977 | Bromberg | 356/339 |
| 4,059,405 | 11/1977 | Sodickson et al. | 422/68 |
| 4,125,828 | 11/1978 | Resnick et al. | 250/461.2 |
| 4,174,952 | 11/1979 | Cannell et al. | 422/73 |
| 4,205,954 | 6/1980 | Babson | 356/339 |
| 4,252,536 | 2/1981 | Kishimoto et al. | 422/73 |
| 4,452,902 | 6/1984 | Suovaniemi et al. | 356/427 |

OTHER PUBLICATIONS

Fisher Scientific 81, 1980, p. 672.

*Primary Examiner*—Barry S. Richman
*Assistant Examiner*—Michael S. Gzybowski
*Attorney, Agent, or Firm*—Blum Kaplan Friedman Silberman & Beran

[57] ABSTRACT

A reagent detection system for detecting an agglutination reaction in a reagent is provided. A light source directs monochromatic light toward an isoplanar sample field. A detector is provided for detecting a change in the amount of light scattered from the isoplanar sample field caused by the agglutination reaction of the reagents. The agglutination reaction is controlled by the intervention of a kinetic activator and results in consistently reproducible sensitive detection of the agglutination reaction.

14 Claims, 14 Drawing Figures

FIG. 5
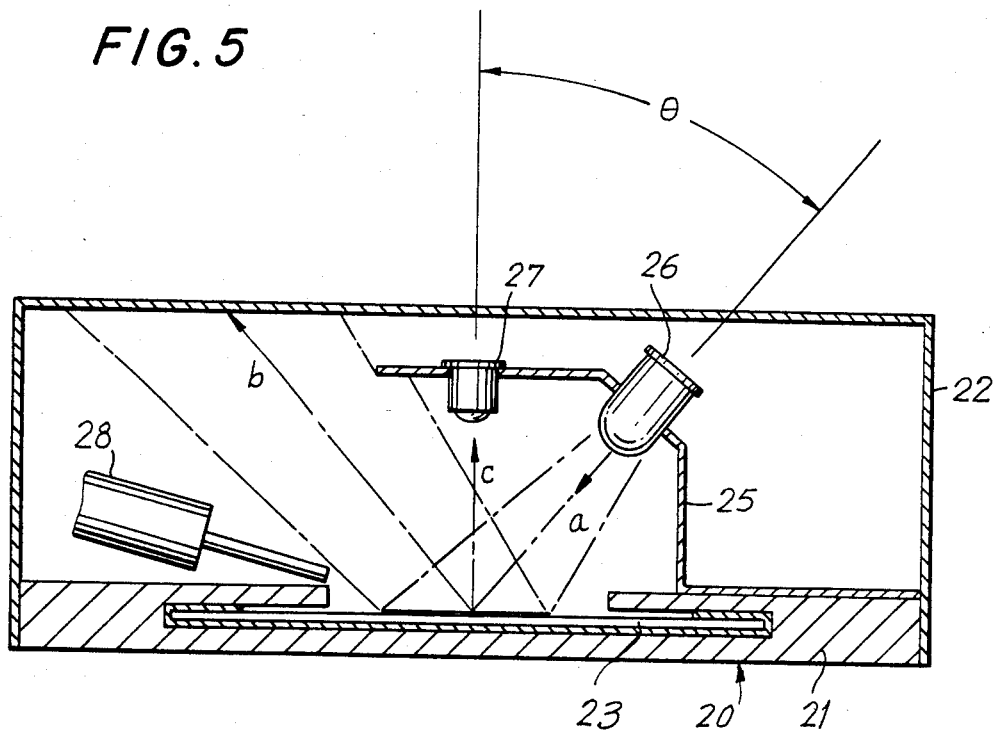
FIG. 6
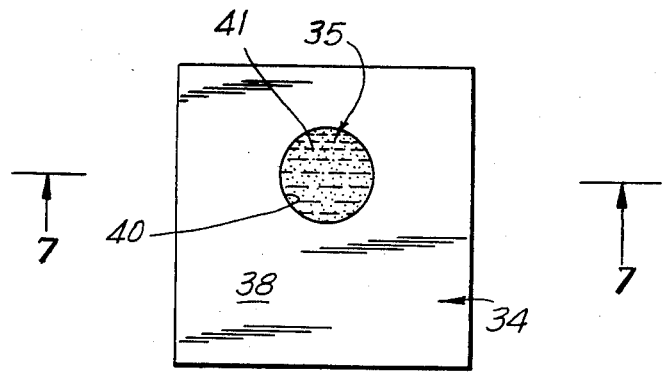
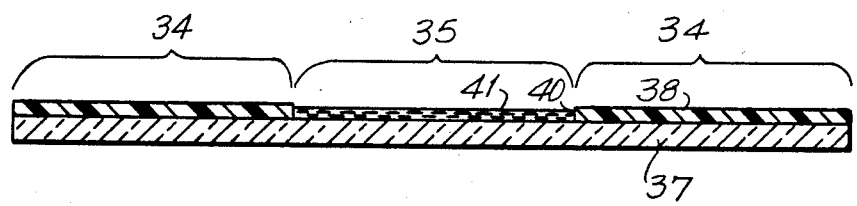
FIG. 7

AGGLUTINATION REAGENT DETECTION SYSTEM

BACKGROUND OF THE INVENTION

This invention is generally directed to a system for controlling and detecting an agglutination reaction and, in particular, to providing a system that creates a controlled isoplanar agglutination reaction that is optoelectronically detected.

Agglutination reagents have been used in recent years for diagnostic test purposes in the immunochemical field. Immunochemical testing is used for detecting certain molecules, the presence of which are indicative of such conditions as human pregnancy, various infectous diseases, allergenic conditions, etc. In testing for the conditions aforenoted, it is desired that objectivity and reproducibility be maximized and subjectivity and nonreproducibility be minimized.

Heretofore neither optimum sensitivity nor reproducibility have been obtainable, by reason of the manner in which such immunoassay reactions have been performed and evaluated. For example, the most common method of testing for conditions using an agglutination reagent is to manually react the reagents on a slide or in a test tube and to evaluate the agglutination reaction (i.e., agglutination or non-agglutination,) with the unaided eye. Such methods of manual testing rely entirely upon the visual acuity of the person doing the testing. Not only is sensitivity and reproducibility not attainable from individual-to-individual, but even the same individual conducting a series of tests cannot eliminate one's inherent subjectivity.

In order to overcome the subjectivity inherent in manually analysing an agglutination test, efforts have been made to lessen the subjectivity of manual testing by the utilization of known instrumentation in the diagnostic field. One such test method uses a spectrophotometer to measure the agglutination reaction in a spectrophotometer cell (a test tube). It is noted however that a standard spectrophotometer cell has a thickness on the order of 1 centimeter (10,000$\mu$). It has been found that known agglutination reagents, when placed in a spectrophotometer cell having a thickness on the order of 1 centimeter, have an optical absorbance that is in excess of the limits of conventional machine readability and, hence, cannot be read by conventional spectrophotometers.

Accordingly, it is necessary to dilute known existing reagents by $10^2$ in order to permit the reagents to be within the range of a spectrophotometer. However, dilution on a magnitude of the type necessary to be readable by a spectrophotometer not only can seriously hamper the sensitivity obtainable by the reaction but also precludes monitoring of a rate reaction on a continuous basis by reason of the intervention necessary to dilute the reagent to obtain a reading by the spectrophotometer. Moreover, an additional disadvantage of using a spectrophotometer is that it only reads the agglutination reaction, if any, that occurs and does not in any way reliably control the reaction conditions and assure repeated reproducibility of the result. Still a further disadvantage of diluting known existing reagents by $10^2$ in order to permit the reagents to be within range of a spectrophotometer is that the speed of the reaction will be greatly reduced many orders of magnitudes to the speed of reaction obtainable when the reagents are not diluted. Accordingly, an agglutination reagent detection system that is capable of controlling the rate of agglutination and is further capable of detecting an agglutination reaction without dilution of the agglutination reagent is desired.

SUMMARY OF THE INVENTION

Generally speaking, in accordance with the instant invention, a reagent detection system for detecting an agglutination reaction in a reagent is provided. The detection system includes a sample field cell for receiving agglutination reagents and defining an isoplanar sample field. A light source directs light toward the isoplanar sample field. A detector detects a change in the amount of light from the isoplanar sample field caused by the agglutination reaction and thereby provides a reproducible and sensitive detection of the agglutination reaction in the sample field.

In addition to the reagent detection system aforenoted, a kinetic energy intervention mechanism can be provided for activating the agglutination reagents in the sample field to thereby control the agglutination reaction. Electronic circuitry can be provided to analyze the controlled rate of reaction and produce readings representative thereof.

Accordingly, it is an object of the instant invention to provide an improved reagent detection system for detecting an agglutination reaction in a reagent.

A further object of the instant invention is to provide a reagent detection system that avoids the necessity of diluting agglutination reagents.

Still a further object of the instant invention is to provide a reagent detection system that provides highly sensitive testing of agglutination reagents on a reproducible basis.

Another object of the instant invention is to provide a reagent detection system that permits the rate of the agglutination reaction to be controlled and measured.

Still other objects and advantages of the invention will in part be obvious and will in part be apparent from the specification.

Ths invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 5 is a cross-sectional elevational view of the reagent detection assembly constructed in accordance with a preferred embodiment of the instant invention;

FIG. 6 is a plan view of a sample cell constructed in accordance with a preferred embodiment of the instant invention;

FIG. 7 is a sectional view taken along line 6—6 of FIG. 6;

DETAILED DESCRIPTION OF THE PREFERRED EMBODIMENTS

Figure 1:
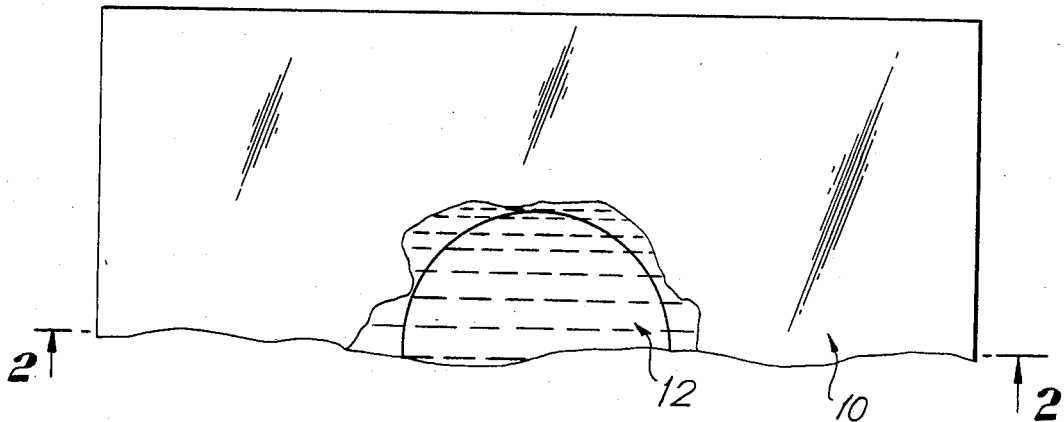
FIG. 1 is a plan view of a sample slide for use in a manual agglutination reagent test in accordance with the prior art.
Figure 2:
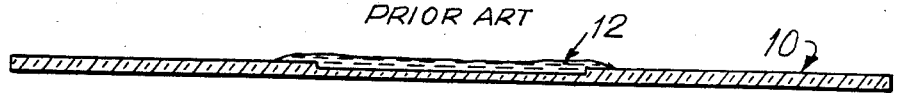
FIG. 2 is a sectional view taken along line 2—2 of FIG. 1.

Reference is first made to FIGS. 1 and 2 wherein a prior art sample slide of the type utilized in the prior art for manual testing of agglutination reactions is depicted. To effect manual testing, an agglutination reagent and test sample are pipetted onto a glass slide 10 having a circular well 11. The mixture of the reagent and test sample define a sample field, generally indicated as 12. By way of background, an agglutination reaction test includes the following basic steps using, as an example, a test for the presence of penicillin in milk as the molecule of interest.

A test sample of 10 μl of filtered milk would be pipetted onto the slide 10. 10 μl of antibody reagent would next be pipetted onto the slide 10. Next, 10 μl of polystyrene latex reagent coated with penicillin is added to the slide 10. All the reagents are then stirred and spread on the slide in the manner illustrated in FIG. 1. The slide is then agitated for several minutes and the sample field on the slide is visually observed, unaided, for the presence of absence of agglutination. If the test sample field is absent the penicillin molecule of interest, a maximum agglutination will occur. If the penicillin molecule of interest is present the agglutination reaction will be inhibited proportionally to the quantity of penicillin present in the milk. Although the absence of presence of penicillin can easily be observed, a quantitative analysis is not attainable by such a manual method. Also, as is explained below, the reaction mixture, as is particularly illustrated in FIGS. 1 and 2, provides an irregular sample field which is non-systematic and thus not reproducible when evaluated by known instrumentation.

Figure 3:
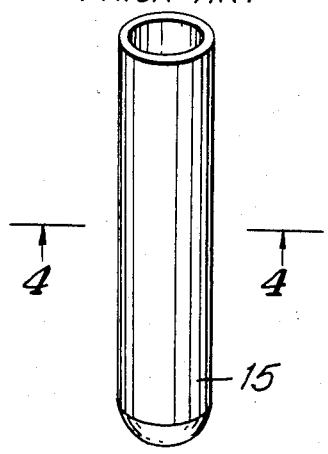
FIG. 3 is an elevational view of a testtube for use in a spectrophotometer agglutination reagent test in accordance with the prior art.
Figure 4:
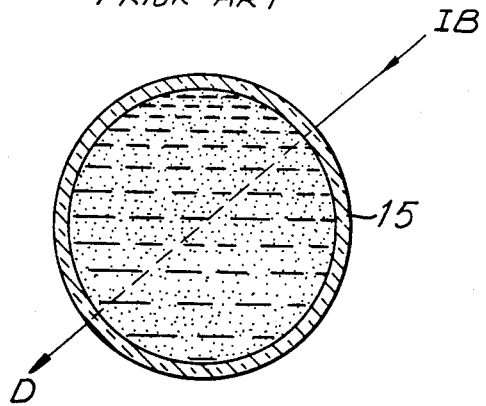
FIG. 4 is a sectional view taken along line 4—4 of FIG. 3.

Reference is next made to FIGS. 3 and 4, wherein a spectrophotometry cell, generally indicated as 15, is illustrated. As is detailed herein, the use of a spectrophotometry cell has been employed to provide quantitative instrument readings of agglutination test reactions.

Using the same example noted above for testing for the presence of absence of penicillin in milk, the same reagents and same test sample are added to the spectrophotometry cell 15, which cell can be on the order of 1 centimeter in sample path dimension. In one known method, the milk is added to the sample cell 15 and the same quantity of antibody and polystyrene latex particles dimensioned on the order of 0.3 to 1.0 microns would also be added to the tube.

The reagents are then reacted by agitation. Next, it is necessary to dilute the reagents in order to bring them into the concentration range of a spectrophotometer, typically 1.0 A (absorbance unit). As is illustrated in FIG. 4, the incident beam IB from a spectrophotometer is directed through the diameter of the sample tube and the exit beam D is detected by a detector diametrically opposed to the source of the incident beam IB. The detector will detect the average amount of light that is passed through the sample, which light represents the average amount of light absorbed by the sample field in the tube 15.

The more penicillin that is present in the milk sample, the less agglutination will occur and, thus, the less amount of light will be detected. Alternatively, if there is substantially no penicillin present in the milk, a greater agglutination reaction will occur, and more light will pass through to the detector. Although it is possible to obtain quantitative readings using spectrophotometry, the sensitivity and speed of the reaction is substantially diminished by reason of the dilution of the reagents in order to accommodate the range of the spectrophotometer.

However, if the reagents in the sample tube are not diluted, multiple scattering causes an attentuation of the detected light and causes the detectable light D to be off-scale for use by the spectrophotometer. In the art, multiple scattering is considered to occur when a 1.0 cm long path has an absorbance greater than 0.1 A (absorbance units). Moreover, in addition to requiring dilution of the test sample, the readings by the spectrophotometer represent the average amount of light transmitted through the sample and does not represent or linearly relate to the number of particles in the test samples. As is demonstrated below, each of the aforenoted disadvantages of the prior art are overcome by the reagent detection system of the instant invention.

Reference is now made to FIG. 5 wherein a reagent detection system, generally indicated as 20, constructed in accordance with the instant invention, is depicted. A slide support base member 21 and a housing 22 define an enclosure for receiving a sample slide. A support bracket 25 positions a light emitting diode 26 at a predetermined position with respect to the sample slide 23 for directing monochromatic light toward the sample slide 23. Support bracket 25 further positions a silicon photodiode detector 27 at a predetermined position with respect to the sample slide 23. An air duct 28 is positioned at an angle incident to the sample slide 23 to apply an air flow across the surface of the sample slide to effect mixing in a manner which is also explained in greater detail below.

Slide support base member 21 is constructed to permit the sample slide 23 to be removably displaced into a position with respect to photodiode detector 27, the incident light produced by light emitting diode 26 and air duct 28. As is illustrated in FIGS. 6 and 7, sample slide 23 includes a non-wettable zone 34 and a wettable zone 35. The slide support 23 positions the sample slide 23 so that light emitting diode 26 directs monochromatic light onto the wettable zone 35. Photodiode detector 27 is positioned above the wettable zone with its access of field of view being normal to the plane of the wettable zone of the sample cell and centered with respect to the geometry of the wettable zone. Air duct 28 is positioned with respect to the wettable zone in order to direct a jet of air onto the wettable zone to activate kinetically the reagents positioned at the wettable zone in a manner which is described in greater detail below.

In order to define a discrete wettable zone and a non-wettable zone, the sample slide 23 is comprised of a glass substrate 37 having a Mylar ® or other plastic or other non-wettable layer 38 bonded thereto. The glass substrate is wettable with respect to the reagent. The wettable zone 35 is formed by including an opening 40 in the non-wettable layer 38. The opening 40 in the non-wettable layer in combination with the surface of the glass substrate 37 that is coextensive with the opening defines a sample cell and, for the reasons described below, provides a test sample field that is "field planar" or "isoplanar". In a preferred embodiment, a non-wettable film layer of Mylar ® having a thickness of $100\mu$ is provided. Although slides having enamel paint coatings of $20\mu$ thickness have been tested, a $100\mu$ to $200\mu$ thickness non-wettable layer is preferable for the volumes of test reagents which are discussed below. In an exemplary embodiment using $1\mu$ particles, the depth of the sample cell is within $100\mu$ to $200\mu$. Nevertheless, it can be appreciated that a sample cell on the order of $100\mu$ to $200\mu$ will assure that a sufficiently isoplanar sample field on the order of $100\mu$ to $200\mu$ will be provided in the sample slide.

As is illustrated in FIG. 7, by providing a non-wettable film on the substrate 37, a circular sample cell 41 containing an isoplanar sample field layer of agglutination reagent in the sample cell is provided. Moreover, as will be explained with respect to FIG. 8a, a sample field having a uniform thickness is not obtainable by merely placing a recess in a wettable surface of the type illustrated in FIGS. 1 and 2. Instead, a 90° contact angle defined by the combination of the non-wettable film 38 on the wettable substrate 37 is necessary to define an isoplanar sample field.

Figure 8A:
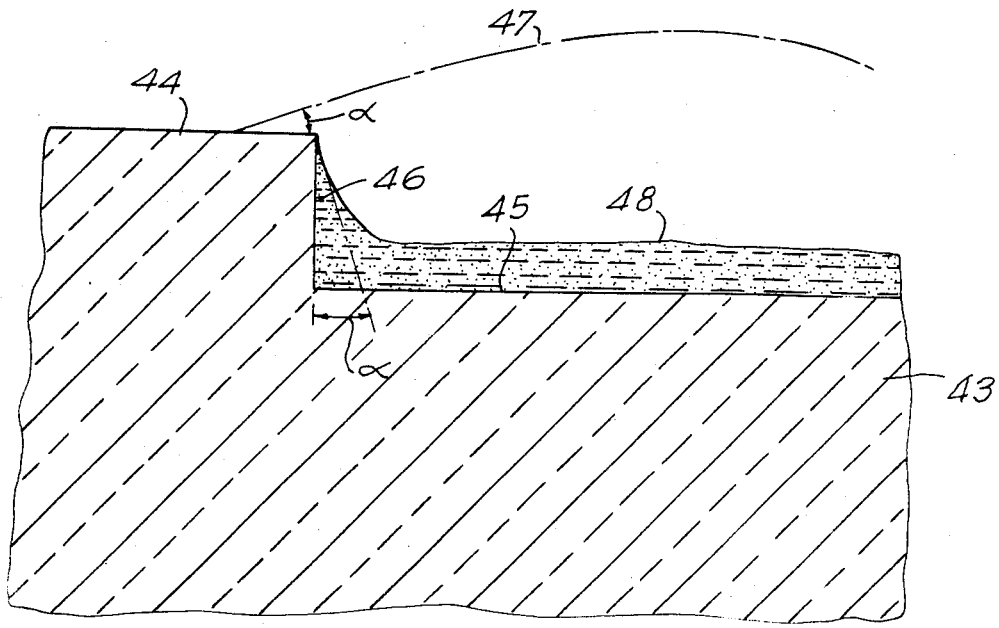
FIGS. 8a and 8b are exploded fragmentary diagramatic illustrations respectively comparing a sample cell in accordance with the prior art with a sample cell constructed in accordance with the instant invention.

FIG. 8a illustrates a blown up portion of the glass slide, depicted in FIG. 1, having a top surface 44 and circular well 11, formed therein. The circular well 11 includes a floor 45 and a wall 46. When the agglutination reagents are added to the well 11, the wettable surface permits an acute angle $\alpha$ to be defined by the liquid. Moreover, as the circular sample cell is filled to overflow, the overflow appears in the manner illustrated in phantom in FIG. 8a, and overflows the circular boundary well in the manner illustrated in FIGS. 1 and 2. An acute angle $\alpha$ is formed by the meniscus of the reagents and the wettable surfaces and prevent a thin isoplanar sample field from being formed.

Figure 8B:
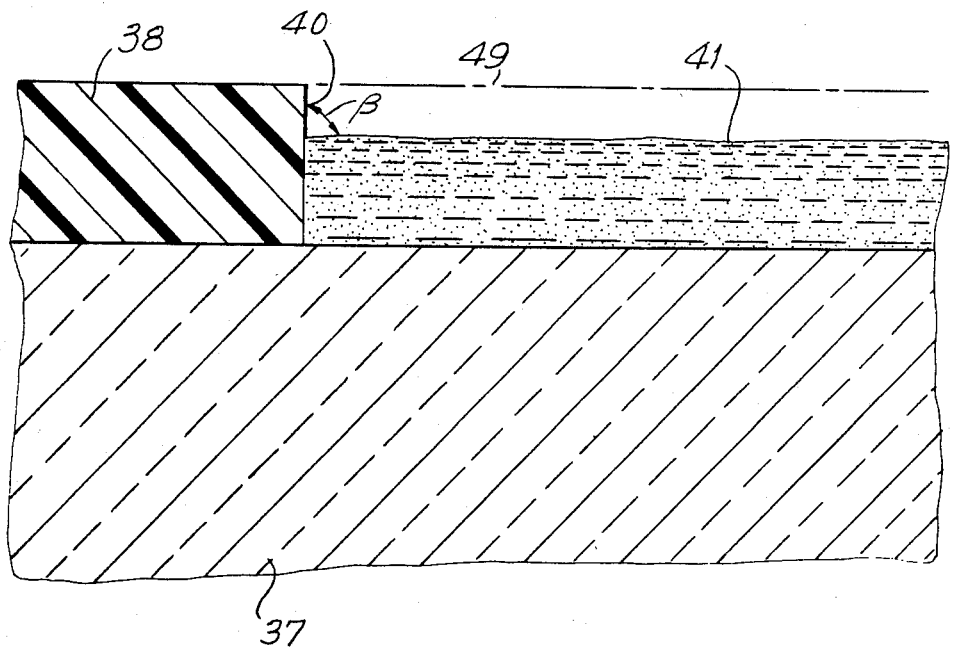

In contrast to FIG. 8a, reference is made to FIG. 8b, wherein blown up portion of the glass slide, illustrated in FIGS. 6 and 7, is depicted, like reference numerals being utilized to denote like elements. Non-wettable film layer 38 is disposed on glass substrate 37. The test sample reagents define a isoplanar sample field 41 which admits of a substantially planar surface. The non-wettable surface 40 of the non-wettable layer 38 causes a 90° contact angle $\beta$ to be defined and causes the sample field of reagents to evenly distribute through the sample cells.

In FIG. 8a, the wettable surfaces defining the sample cause the reagent mixture to form a meniscus which, in turn, causes the acute angles aforenoted and thus bulges and recesses. In contrast thereto, the non-wettable layer 38 prevents creeping of the liquid out of the wettable zone and causes a surface tension film that parallels the plane of the wettable zone to be formed. By creating a planar thin film reagent sample field in the sample cell, the sample field can provide a highly stabilized and reproducible optical field and provides for reproducible kinetic activation.

In an exemplary embodiment the optical field radius equals 7302.5 microns and the particles in the reagents are used to scatter light in a single scattering or isoplanar mode. As has been explained herein, the term "isoplanar" is used to define the manner in which all the particles in the sample cell are seen by the detector as existing in the same plane.

Referring again to FIG. 5, the light emitting diode 26 directs monochromatic light at the isoplanar sample field. In a preferred embodiment monochromatic light is directed at an incident angle $\theta$ which is 40° relative to the axis of the photodiode detector 27. As aforenoted, detector 27 is disposed normal to the isoplanar sample field of the reagents formed in the sample cell. When incident beam A is projected onto the sample field, a portion of the incident light is reflected in direction B and is not read by the detector 27. However, a small portion of the incident light beam is scattered by the particles in the sample cell and is read by photodiode detector 27. As will be explained in detail below, because of the isoplanar sample field of reagents, each particle in the sample cell individually scatters light directly back to the photodiode detector 27.

Figure 9A:
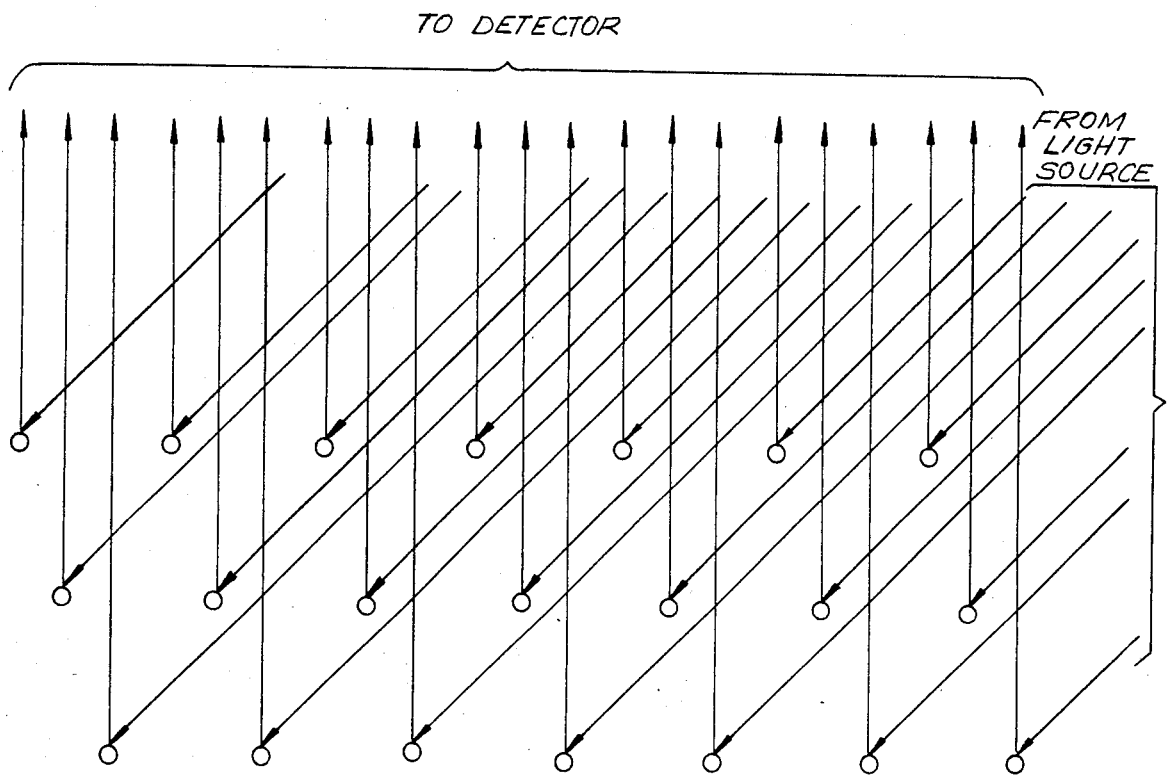
FIGS. 9a and 9b are diagramatic illustrations of the manner in which an agglutination reaction is detected by the agglutination reagent detection system of the instant invention.

This scattering effect is illustrated in FIG. 9a which represents an isoplanar sample field, in accordance with the instant invention, having non-agglutinated particles. Light enters from the light source at an angle $\theta$ and a small portion of the light incident thereon is scattered to the detector, which is normal to the sample cell. In FIG. 9a, a considerable amount of light is scattered to the detector.

Figure 9B:
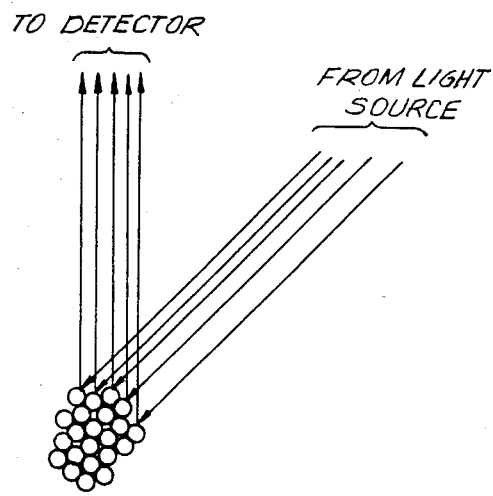
Figure 10:
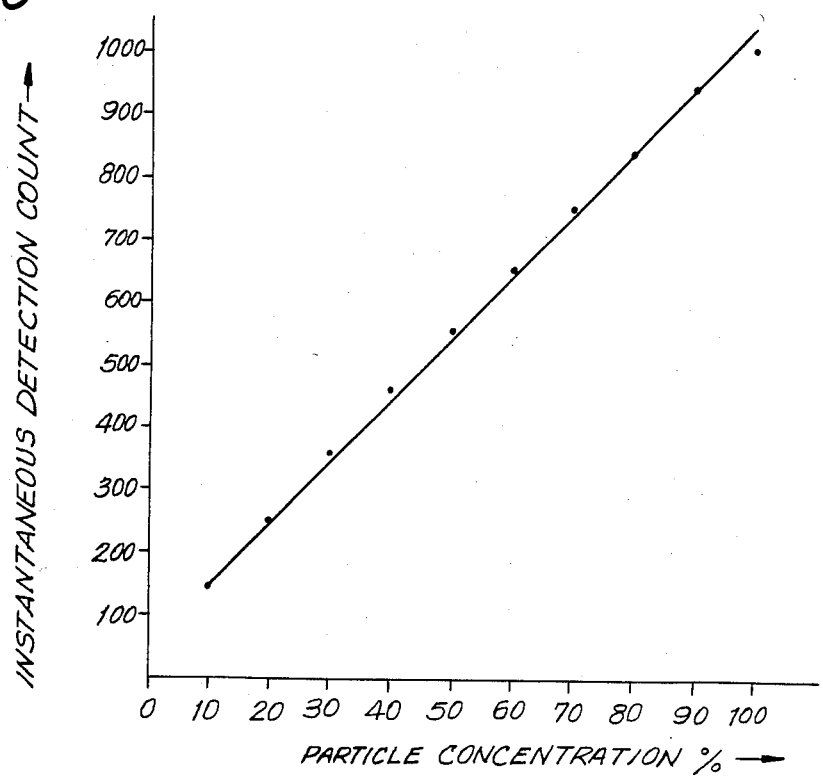
FIG. 10 is a graphical illustration comparing the output level of the detection system to particle concentration and the linear relationship therebetween.

In FIG. 9b, when the particles in the sample zone are agglutinated, they coalesce or clump in a single area or in several distinct areas. Because of the clumping, only a small amount of light is scattered to the detector. Although the detector is looking at the same isoplanar sample field, the amount of light scattered back and seen by the detector is substantially reduced. By instantaneous summing the light scattered from substantially all of the individual particles, the detector is capable of providing a voltage that is linearly proportional to the number of particles detected. To this end, FIG. 10 illustrates a graphical comparison of the instantaneous detector output count to particle concentration and demonstrates the manner in which the detector of the instant invention provides an analog signal which is linearly summed based upon the isoplanar field of detection. In this regard, reagents on the order of 100 A (absorbance units) and higher have been readily detected by the instant invention. Moreover, by using the instant invention, it is not necessary to dilute the reagent in order to obtain instrument readings and a direct reading or summing of the particles is created in contrast to the light averaging that is characterized by the use of a spectrophotometer.

Again, returning to FIG. 5, the reagent detection system not only provides for a substantially direct reading, summing or counting of the particulate subject matter, but further is able to control the rate of the reaction and thus provide highly sensitive and reproducible data. As was noted above with respect to the prior art, agglutination reactions result from an agitation of the reagents after mixing. For this reason, air duct 28 is positioned to kinetically activate the reagents in the sample cell and thereby assure that the reaction has sufficiently progressed before being read by the detector.

Figure 11:
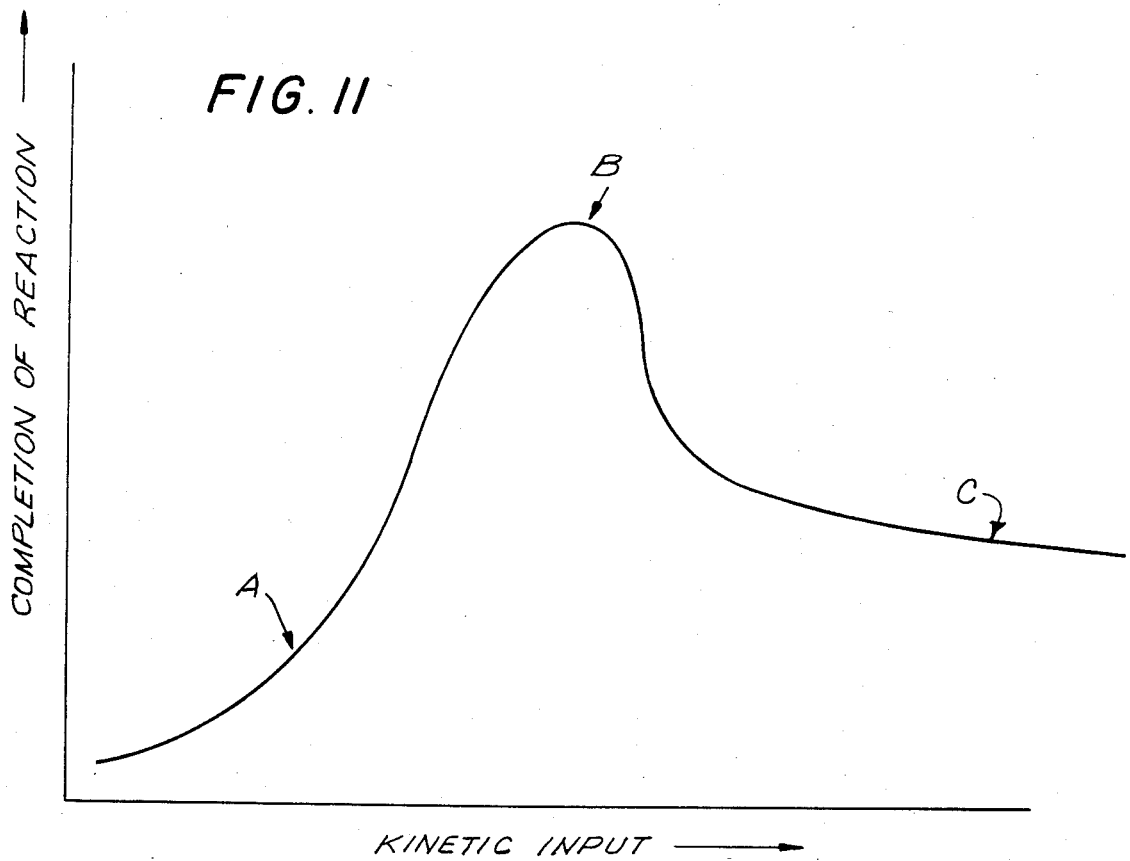
FIG. 11 is a graphical illustration depicting the kinetic energy necessary to control an agglutination reaction in accordance with the instant invention.
Figure 12:
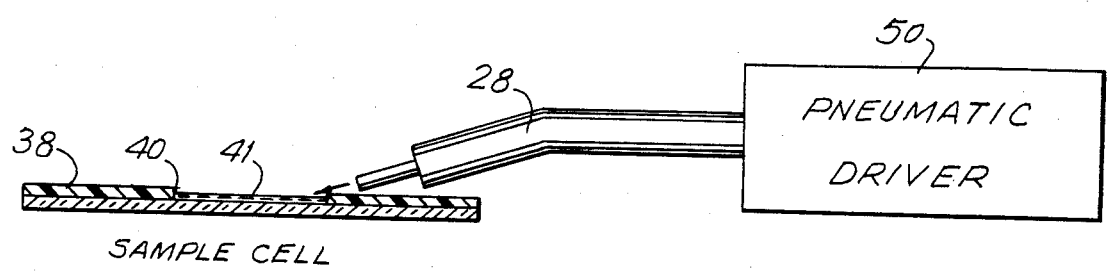
FIG. 12 is an illustration of the kinetic activator system of the instant invention.
Figure 13:
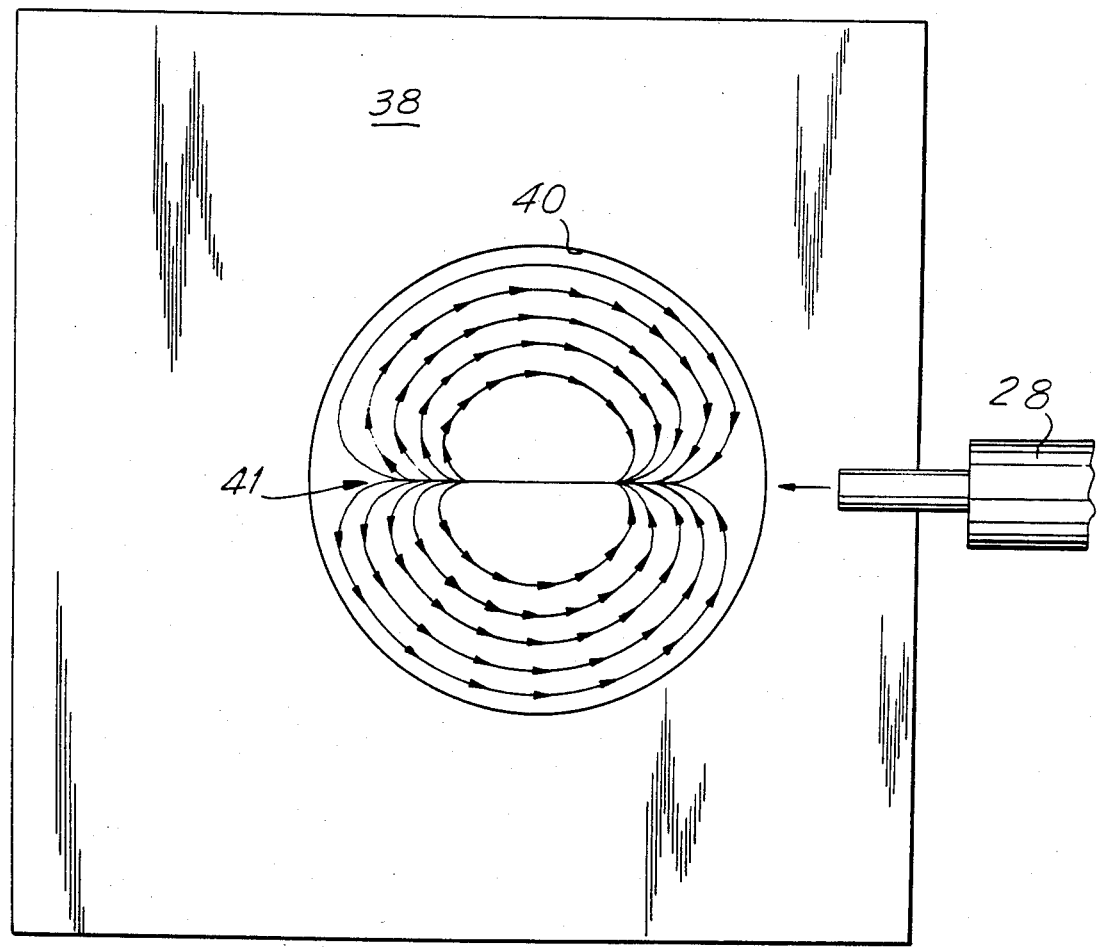
FIG. 13 is a diagramatic illustration of the movement of particles in the sample cell by the kinetic activator system of the instant invention.

As is illustrated in FIGS. 11 through 13, a digitally controlled pneumatic driver 50 applies an air jet through duct 28 to the reagents in the sample cell 41. By using an air jet, no other elements, including the sample slide, need be moved and yet a sufficient amount of energy can be introduced to overcome inertia and accelerate all of the particles in the agglutination reaction toward each other. Such acceleration causes the particles to move within a critical distance of each other for the immuno-reagent to react. It has been observed that if the acceleration is too strong (C) or if too little energy is provided (A), the reaction does not go to completion. This relationship is illustrated in FIG. 11 and demonstrates that an optimal kinetic input (B) can be selected.

In order to obtain an ideal movement of the reagent, repetitive impulses of air are directed by the air duct over the isoplanar sample field of the reagents in the sample cell, to thereby establish toroidal counter revolving currents. A current flow, of the type illustrated in FIG. 14, accelerates the particles toward one another continuously at point A by directing the impulses of air at point A. The particles are also removed from point A and randomly distributed about the sample cell in a continuous toroidal counter revolving motion. Kinetic activation, of the type illustrated in FIG. 13, permits the greatest number of particles to react with each other in a statistically random manner and yields an optically uniform and reproducible sample. By reason of the optical uniformity and reproducibility of the sample, increased sensitivity of the immuno chemical reagent results and, hence, more sensitive detection is obtained. Although the use of a pneumatic driver to kinetically activate the sample field results in a uniformly reproducible reaction and is preferred, other kinetic activation mechanisms can be used to otherwise sufficiently agitate the sample field.

Figure 14:
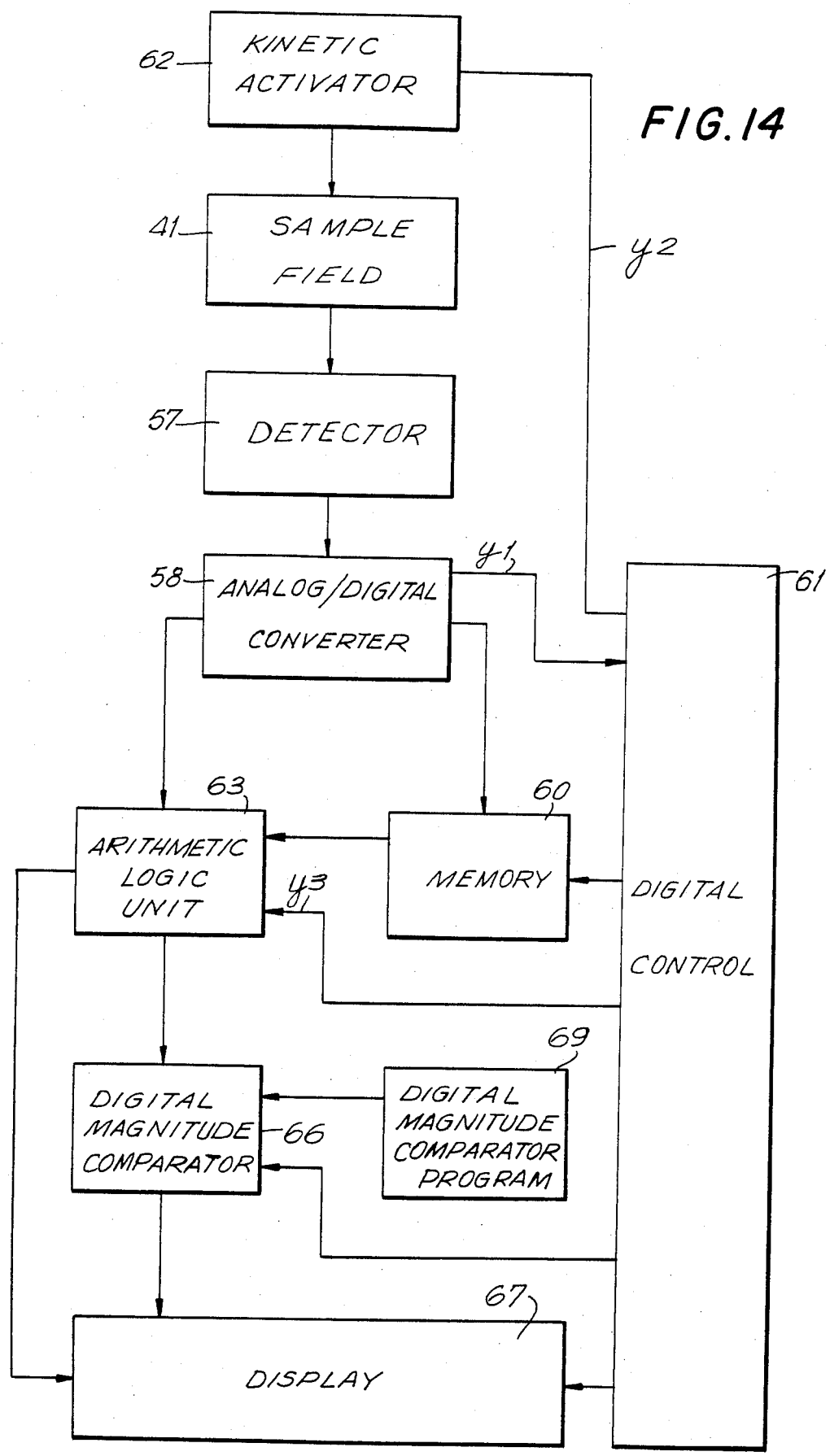
FIG. 14 is a block circuit diagram of the reagent detection circuit used with the reagent detection assembly illustrated in FIG. 5.

Referene is next made to FIG. 14, wherein a block circuit diagram of the electronic system used to produce a display representative of the detection of the agglutination reaction is depicted, like reference numerals being utilized to denote like elements depicted above. Detector circuit 57 includes photodiode detector 27 and produces an analog signal representative of the amount of agglutination detected. When an isoplanar sample field 41 is placed in a sample cell, detector circuit 57 produces an initial analog signal representative of the initial condition of the agglutination reaction (FIG. 9a). The initial analog signal produced by detector 57 is converted by analog-to-digital circuit 58 and is stored in memory 60. Coincident with the storage of the initial digital signal in the memory 60, analog-to-digital circuit 58 supplies a first control signal $\Psi 1$ to the digital control circuit. In response to control signal $\Psi 1$ digital control circuit 61 applies a second control signal $\Psi 2$ to kinetic activator circuit 62, which circuit causes pneumatic driver 50 to affect air impulses to be directed at the sample field and to cause reagent movement of the type illustrated in FIG. 13. After a fixed number of kinetic impulses, kinetic activation is stopped.

Detector circuit 57 next reads the agglutination reaction in the sample cell which represents a summing of the particles (FIG. 9b) and a digital signal representative of this second reading is again applied by analog-to-digital converter 58 to the arithmetic logic circuit 63. Next, digital controla signal $\Psi 3$ is applied to arithmetic logic unit 63 which effects a subtraction of the second digital number from the first digital number stored in memory 60. A signal representative of the difference in voltage per differene in kinetic energy (dK/dV) where dv equals the difference in the detector output voltage per the difference in the kinetic energy (dK) of the reaction is provided. This result (dV/dK) can then be produced in a three digital quantitative format and directly applied to a digital display 67. Alternatively, display 67 can be a plus (+) or − (minus) display and a digital magnitude comparator 66 and a soft-ware program 69 can be used to produce a yes (+) or no (−) signal to the display 67.

Thus, the instant invention is capable of providing an output count representative of particle concentration or, alternatively, if suitably programmed a plus or minus result. If a test is made of a quantitative nature, the reagent detection system of the instant invention is capable of providing a numerical representation. On the other hand, if the test being performed by the agglutination reagent is one which only requires a yes or no answer, such as a positive pregnancy test, a plus or minus response would be sufficient for the purposes intended and would eliminate the necessity of incorporating in the second circuit a digital display.

The instant invention is, thus, particularly characterized by the combination of an isoplanar sample field that has a 90° angle that is effected by the combination of a non-wettable surface and wettable surface for defining a sample cell and detection of scattered incident light in order to linearly sum the particulate reaction and, thereby, provide improved sensitivity. The instant invention is further characterized by the use of kinetic activation means for agitating the reagents in the sample cell to control the rate of agglutination and, thereby, assure that the results of each test are readily reproducible. Moreover, each of the features above are readily integrated into an electro optical instrument that is capable of providing a differential reading based upon difference in the detector output voltage in light of the difference in the kinetic energy of the reaction to provide differential data which yields results which are a magnitude higher in sensitivity and resolution to those heretofore obtained by manual methods. Moreover, such sensitivity is obtained using reagents having an absorption level on the order of 100 A (absorbance units) thereby avoiding the necessity of diluting the reagents for use in an instrument such as a spectrophotometer and the resultant loss of efficacy of the reagents which results therefrom.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A reagent detection system for detecting a particulate agglutination reaction in an reagent comprising, in combination, sample field means for receiving a particulate liquid agglutination reagent and defining a liquid isoplanar sample field, light means for directing light towards said liquid isoplanar sample field, and detection means cooperating with said light means for instantaneously detecting a change in the amount of light scattered from said liquid isoplanar sample field caused by the agglutination reaction by summing light scattered from substantially all particles in the sample field and in response thereto for producing a display signal that is substantially linearly related to the surface area of the particles as modified by agglutination.

2. A reagent detection system, as claimed in claim 1, and including kinetic energy activation means for kinetically activating said liquid sample reagent in said sample field to thereby control the agglutination reaction caused thereby.

3. A reagent detection system, as claimed in claim 2, wherein said kinetic activation means kinetically activates said reagents for a predetermined interval of time to define a controlled reaction, said detection means being adapted to detect said reagent at the beginning and at the end of said predetermined interval.

4. A reagent detection system, as claimed in claim 1, 2 or 3, wherein said sample field means for receiving said reagents and defining said liquid isoplanar sample field includes a wettable surface means having a discrete area, said detection means being adapted to detect said light scattered from said discrete area.

5. A reagent detection system, as claimed in claim 4, wherein said light means is a monochromatic light source, said monochromatic light source directing light at said entire discrete area defining said liquid isoplanar sample field.

6. A reagent detection system, as claimed in claim 5, wherein said detection means is positioned normal with respect to said isoplanar sample field and is centered with respect to said discrete area defining said isoplanar sample field.

7. A reagent detection system as claimed in claim 6, wherein said monochromatic light source is disposed at an angle with respect to said detection means to effect detection of a single scattering effect by said detection means.

8. A reagent detection system, as claimed in claim 6, wherein said monochromatic light source is disposed to direct monochromatic light at an angle of 40° with respect to the position defined by positioning of said detection means with respect to said discrete area.

9. A reagent detection system, as claimed in claim 3, wherein said display signal produced by said detection means includes a first analog signal that is representative of the state of the agglutination reaction of the reagent in the liquid isoplanar sample field at the beginning of said predetermined interval and said display signal further includes a second analog signal representative of the state of the agglutination reaction of said reagent in the liquid isoplanar sample field at the end of said predetermined interval of time.

10. A reagent detection system, as claimed in claim 9, and including comparator means for comparing said first analog signal and said second analog signal and for producing a comparative signal representative of any change in level between said first analog signal and said second analog signal.

11. A reagent detection system, as claimed in claim 10, and including display means for receiving said comparative signals and providing a display representative of one of the difference and lack of difference between the level of said first analog signal and said second analog signal.

12. A reagent detection system, as claimed in claim 2 or 3, wherein said kinetic activation means is an air jet for directing air impulses at a predetermined position of said liquid isoplanar sample field to effect movement of said reagent in a predetermined manner.

13. A reagent detection system, as claimed in claim 12, wherein said detection means is adapted to produce a first analog signal that is representative of the state of the agglutination reaction of the reagent in the liquid isoplanar sample field at the beginning of said predetermined interval of time and said detection means is further adapted to produce a second analog signal representative of a second state of the agglutination reaction of said reagent in the liquid isoplanar sample field at the end of said predetermined interval of time.

14. A reagent detection system, as claimed in claim 13, and including comparator means for comparing said first analog signal and said second analog signal and for producing a comparative signal representative of the change in level between said first analog signal and said second analog signal, said signal being representative of the difference in the voltage level of said first analog signal and said second analog signal as compared to the amount of kinetic activation of said reagent in said liquid isoplanar sample field during said predetermined interval of time.

* * * * *

UNITED STATES PATENT AND TRADEMARK OFFICE
CERTIFICATE OF CORRECTION

PATENT NO. : 4,597,944
DATED : July 1, 1986
INVENTOR(S) : Hugh V. Cottingham

It is certified that error appears in the above-identified patent and that said Letters Patent is hereby corrected as shown below:

Title page:

Change "[21] Appl. No.: 542,846" to -- [21] Appl. No.: 542,946 --.

Signed and Sealed this

Twenty-third Day of September 1986

[SEAL]

Attest:

DONALD J. QUIGG

Attesting Officer

Commissioner of Patents and Trademarks